United States Patent [19]
Powers et al.

[11] Patent Number: 4,596,822
[45] Date of Patent: Jun. 24, 1986

[54] HETEROCYCLIC INHIBITORS OF SERINE PROTEASES

[75] Inventors: James C. Powers, Atlanta, Ga.; Wade Harper, Brighton, Mass.

[73] Assignee: Georgia Tech Research Corporation, Atlanta, Ga.

[21] Appl. No.: 642,995

[22] Filed: Aug. 20, 1984

[51] Int. Cl.$^4$ .......................... A61K 31/35; C12N 9/99
[52] U.S. Cl. ..................................... 514/459; 435/184; 514/431; 514/460
[58] Field of Search ....................... 424/281, 279, 275; 435/184; 514/459, 460, 431

[56] References Cited
U.S. PATENT DOCUMENTS
4,036,964  7/1977  Buckle et al. ....................... 424/258

OTHER PUBLICATIONS

Chemical Abstracts (Waki et al.) 95:161781g (1981).
Davies and Poole, J. Chem. Soc., pp. 1616–1629 (1928).
Milevskaya, Belinskaya, and Yagupol'skii, Zhur. Org. Khim 9, pp. 2145–2149 (1973).
Tirodkar and Usgaonkar, Ind. J. Chem. 7, pp. 1114–1116 (1969).
Choksey and Usgaonkar, Ind. J. Chem. 14B, pp. 496–598 (1976).
Knott, J. Chem. Soc., pp. 402–410 (1963).
Powers, Ad. in Chem., 198, pp. 347–367 (1982).

*Primary Examiner*—Leonard Schenkman
*Attorney, Agent, or Firm*—Newton, Hopkins & Ormsby

[57] ABSTRACT

Certain novel heterocyclic compounds, their preparation, and their use in inhibiting serine proteases with chymotrypsin-like, elastase-like, and trypsin-like specificity and in the treatment of diseases such as emphysema which involve tissue proteolysis.

2 Claims, No Drawings

HETEROCYCLIC INHIBITORS OF SERINE PROTEASES

BACKGROUND OF THE INVENTION

This invention relates to a novel class of heterocyclic compounds useful for selectively inhibiting elastase, selectively inhibiting chymotrypsin-like enzymes, selectively inhibiting trypsin-like enzymes, or for generally inhibiting serine proteases of all classes. Certain clinical symptoms found in pancreatitis, emphysema, rheumatoid arthritis, inflammation, and adult respiratory distress syndrome are believed to be caused by uncontrolled elastase in the affected tissues. Likewise, similar clinical symptoms found in the same diseases are believed to be caused by uncontrolled cathepsin G, mast cell chymase, and other chymotrypsin-like enzymes. In vitro, proteolysis by serine proteases of the elastase, chymotrypsin, and trypsin families is often a severe problem in the production, isolation, purification, transport and storage of valuable peptides and proteins.

It is an object of this invention to find a novel group of specific inhibitors for elastase, chymotrypsin, trypsin, and other serine proteases of similar substrate specificity, and serine proteases in general. Inhibitors are substances which reduce or eliminate the catalytic activity of enzymes. Chymotrypsin and chymotrypsin-like enzymes normally cleave peptide bonds in proteins and peptides where the amino acid residue on the carbonyl side of the split bond ($P_1$ residue) is typically Trp, Tyr, Phe, Met, Leu or other amino acid residues which contain aromatic or large alkyl side chains. Elastase and elastase-like enzymes, on the other hand, cleave peptide bonds where the $P_1$ amino acid residue is much smaller, typically Ala, Val, Ser, Leu and other similar amino acids. Trypsin-like enzymes hydrolyze peptide bonds where the $P_1$ amino acid is Lys or Arg. All of the above enzymes have extensive secondary specificity and recognize amino acid residues removed from the $P_1$ residue. The inhibitors of this invention would be useful for treating diseases such as pancreatitis, emphysema, rheumatoid arthritis, adult respiratory distress syndrome, and inflammatory diseases which involve destruction of tissue by serine proteases. In some cases, it would be more useful to utilize a specific elastase, trypsin or chymotrypsin-like enzyme inhibitor, while in other cases an inhibitor with broader specificity would be appropriate.

It is an object of this invention to find a novel group of specific inhibitors useful in vitro for inhibiting elastase, trypsin, chymotrypsin and other serine proteases of similar specificity, and for inhibiting serine proteases in general. Such inhibitors could be used to identify new proteolytic enzymes encountered in research. They could also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts, or other proteins which are widely sold for use in clinical analysis, biomedical research, and for many other reasons. For some uses a specific inhibitor would be desirable, while in other cases, an inhibitor with general specificity would be preferred.

DETAILED DESCRIPTION OF THE INVENTION

Certain substituted isocoumarins have been found to be excellent inhibitors of a number of serine proteases including human leukocyte elastase, porcine pancreatic elastase, bovine chymotrypsin, human cathepsin G, various human and bovine blood coagulation enzymes, human complement factor D, and several mammalian mast cell proteases. These compounds inhibit the serine proteases by acylating the active site serine residue and in some cases form an additional covalent bond. These structures may be used in vivo to treat diseases resulting from tissue destruction due to elastase, chymotrypsin, trypsin, and related enzymes. They may be used in vitro to prevent proteolysis that occurs during the production, isolation, purification, storage, and transport of peptides and proteins. The novel substituted isocoumarins and related heterocyclic analogs have the following structural formula:

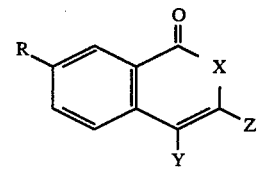

wherein

X is selected from the group consisting of O and S,

Z is selected from the group consisting of H, halogen, $C_{1-6}$ alkyl, $C_{1-6}$ alkyl with an attached phenyl, $C_{1-6}$ fluorinated alkyl, $C_{1-6}$ alkoxy, $C_{1-6}$ fluorinated alkoxy, $C_{1-6}$ alkoxy with an attached phenyl, benzyloxy, 4-fluorobenzyloxy, $-OCH_2C_6H_5-R'$ (2-substituent), $-OCH_2C_6H_5-R'$ (3-substituent), $-OCH_2C_6H_5-R'$ (4-substituent), $-OCH_2C_6H_4-R_2'$ (2,3-substituents), $-OCH_2C_6H_4R_2'$ (2,4-substituents), $-OCH_2C_6H_4R_2'$ (2,5-substituents), $-OCH_2C_6H_4-R_2'$ (2,6-substituents), $-OCH_2C_6H_4-R_2'$ (3,4-substituents), and $-OCH_2C_6H_4-R_2'$ (3,5-substituents), R' is selected from the group consisting of H, halogen, trifluoromethyl, $NO_2$, cyano, methyl, methoxy, acetyl, carboxyl, OH, and amino, Y is selected from the group consisting of H, halogen, trifluoromethyl, methyl, OH, and methoxy, R is selected from the group consisting of H, OH, $NH_2$, $NO_2$, halogen, $-NH-C(NH)-NH_2$, $-C(NH)N_2$, $C_{1-6}$ alkoxy, $C_{1-6}$ fluorinated alkoxy, $C_{1-6}$ alkyl, $C_{1-6}$ alkylamino, M-AA, and M-NH, wherein AA is selected from the group consisting of alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, alpha-aminobutyric acid, epsilon-aminocaproic acid, citrulline, hydroxyproline, ornithine, and sarcosine, wherein M is selected from the group consisting of hydrogen, lower alkanoyl having 1 to 6 carbons, carboxylalkanoyl, hydroxyalkanoyl, amino-alkanoyl, benzene sulfonyl, tosyl, benzoyl, and lower alkyl sulfonyl having 1 to 6 carbons.

Several of these compounds have been prepared earlier for other purposes (illustrative examples: Davies and Poole, J. Chem. Soc., pp 1616–1629, (1928); Milevskaya, Belinskaya, and Yagupol'skii, Zhur. Org. Khim.

9, pp 2145-2149, (1973); Tirodkar and Usgaonkar, Ind. J. Chem. 7, pp 1114-1116, (1969); Choksey and Usgaonkar, Ind. J. Chem. 14B, pp 596-598, (1976)).

The following compounds are representative of the invention:
3-chloroisocoumarin,
3,4-dichloroisocoumarin,
3-ethoxy-4-chloroisocoumarin,
3-isobutyloxy-4-chloroisocoumarin,
3-benzyloxy-4-chloroisocoumarin,
3-(4-fluorobenzyloxy)-4-chloroisocoumarin,
7-amino-3-methoxy-4-chloroisocoumarin,
7-amino-3-ethoxy-4-chloroisocoumarin,
7-amino-3-benzyloxy-4-chloroisocoumarin,
7-nitro-3-methoxy-4-chloroisocoumarin,
7-nitro-3-ethoxy-4-chloroisocoumarin,
7-nitro-3-benzyloxy-4-chloroisocoumarin,
7-hydroxy-3-ethoxy-4-chloroisocoumarin,
7-nitro-3-methoxyisocoumarin,
7-nitro-3-(2-phenethoxy)-4-chloroisocoumarin,
7-amino-3-(2-phenethoxy)-4-chloroisocoumarin, and
7-(N-tosyl-phenlyalanylamino)-4-chloro-3-methoxyisocoumarin.

When R is H, $NH_2$, $NO_2$, X is O, and Y and Z are any of the noted groups, the isocoumarin structure is a general inhibitor for both human leukocyte (HL) elastase and bovine chymotrypsin. Although these substituted isocoumarins are slightly less effective toward porcine pancreatic (PP) elastase and cathepsin G, they are still capable of inhibiting these enzymes. The rate constants for inactivation of HL elastase, PP elastase, and chymotrypsin by 3-chloroisocoumarin (X=O, Z=Cl, and Y=H) have been measured and are published, (Harper, Hemmi, and Powers, J. Amer. Chem. Soc. 105, pp 6518-6520 (1983)). 3-chloroisocoumarin also inactivates rat mast cell proteases I and II and *Streptomyces griseus* protease A with rates of 84, 85, and 196 $M^{-1} s^{-1}$, respectively. Rate constants for inactivation of a number of elastase, chymotrypsin, and trypsin-like enzymes by 3,4-dichloroisocoumarin (R=H, X=O, Y=Z=Cl) are given in Table I. This table indicates the generality of this compound as a serine protease inhibitor.

TABLE I

Inactivation of Proteases by 3,4-Dichloroisocoumarin[a].

| Enzyme | Inhibitor Concentration (μM) | $t_{\frac{1}{2}}$ (min) | $k_{obsd}/[I]$ ($M^{-1}s^{-1}$) |
|---|---|---|---|
| Human Leukocyte Elastase[b] | 1.1 | 1.2 | 8920 |
| Porcine Pancreatic Elastase | 8.1 | 0.57 | 2500 |
| Human Leukocyte Cathepsin G | 49.0 | 8.4 | 28 |
| Rat Mast Cell Protease I | 38.0 | 1.2 | 259 |
| Rat Mast Cell Protease II[b] | 11.0 | 1.8 | 583 |
| Human Skin Chymase | 92.0 | 4.7 | 27 |
| Bovine Chymotrypsin-A | 13.0 | 1.6 | 566 |
| S. griseus Protease A | 136.0 | 0.3 | 306 |
| Subtilisin | | | substrate |
| Human Thrombin[c] | 340.0 | 3.4 | 10 |
| Bovine Thrombin | 127.0 | 3.7 | 25 |
| Human Plasmin | 203.0 | 0.4 | 133 |
| Porcine Pancreatic Kallikrien[c] | 127.0 | 3.4 | 27 |
| Bovine Factor Xa[c] | 422.0 | 133.0 | 0.2 |
| Bovine Factor XIa[c] | 239.0 | 1.8 | 27 |
| Human Factor XIIa[c] | 135.0 | 1.3 | 64 |
| Human Factor D | 109.0 | 0.6 | 192 |
| Bovine Trypsin | 127.0 | 0.5 | 198 |
| S. aureus Protease V-8[e] | 18.0 | 0.3 | 2765 |
| Acetylcholinesterase[f] | 157.0 | >120 | <0.6 |
| Beta-Lactamase[f] | 385.0 | | NI[g] |
| Papain[h] | 422.0 | | NI |
| Leucine aminopeptidase[e] | 400.0 | | NI |

[a]Inactivation measurements were performed using the incubation method in 0.1 M Hepes, 0.5 M NaCl, 8-10% Me$_2$SO, pH 7.5 using the incubation method. An aliquot of inhibitor was added to an enzyme solution and aliquots removed with time and assayed for remaining enzymatic activity. First order rate constants, $k_{obsd}$, were obtained from the slope of plots of ln ($v/v_o$) versus times.
[b]Data obtained by progress curve method of Tian and Tsou, Biochemistry 21, 1028-1032, (1982).
[c]Incubation and assay buffer was 0.1 M Hepes, 5 mM CaCl$_2$, 8-10% Me$_2$SO, pH 7.5.
[d]Data obtained using the progress curve method (0.1 M Hepes, 5 mM CaCl$_2$, 10% Me$_2$SO, pH 7.5).
[e]Buffer was 0.1 M Hepes, 10% Me$_2$SO, pH 7.5.
[f]Buffer was 0.1 M phosphate, 10% Me$_2$SO, pH 7.0.
[g]NI, no inactivation.
[h]Buffer was 0.05 M Tris HCl, 5 mM cysteine, 2 mM ethylenediaminetetraacetic acid, 10% Me$_2$SO, pH 8.2.

Table II shows the inactivation rate constants for several serine proteases inhibited by substituted 3-alkoxyisocoumarins. These $k_{obsd}/[I]$ values are second order inactivation rate constants and reflect irreversible inactivation of the enzyme. In some cases (see Tables I and II), inactivation rate constants were measured in the presence of substrate using the progress curve method as described by Tian and Tsou, Biochemistry 21, pp 1028-1032, (1982). Significant, and in most cases total, inactivation of the enzyme will occur if the inhibitor concentration is chosen to be 5 to 50 times the enzyme concentration. The 7-amino-4-chloro-3-methoxyisocoumarin is an essentially stoichiometric inactivator of PP elastase and chymotrypsin.

The rate at which the enzyme is inactivated can be altered by changing both R, Z, and Y. The structures with long alkoxy or benzyloxy substituents are best at inhibiting chymotrypsin, while the most effective HL elastase inhibitors contain Z groups of Cl and $C_{1-4}$ alkyloxy. Isocoumarin itself (X=O, Z=Y=H, and R=H) does not inhibit serine proteases. One of the most effective inhibitors of the blood coagulation proteases and other trypsin-like enzymes was 3,4-dichloroisocoumarin (Z=Y=Cl, R=H, X=O). Attachment of positively charged groups such as guanidine or amines in R or Z would make the inhibitor reactive towards trypsin-like enzymes. Additional specificity towards a particular protease could be achieved by the placing the proper aminoacid or peptide derivative on the 7-amino group. Thus the specificity or generality of the inhibition reaction can be controlled first, by choosing the appropriate inhibitor structure and second, by choosing the inhibitor concentration utilized.

TABLE II

Rate Constants ($k_{obsd}/[I]$) for Inactivation of Serine Proteases by Substituted-4-chloroisocoumarins[a].

| Inhibitor | Enzyme | | | | | |
|---|---|---|---|---|---|---|
| | HLE[b] | PPE[c] | Cat G[d] | ChyT[e] | RMCP II[f] | SGPA[g] |
| 3-ethoxy-4-chloro- | 43000[h] | 940 | 190 | 610 | 3050 | 820 |

TABLE II-continued

Rate Constants ($k_{obsd}/[I]$) for Inactivation of Serine Proteases by Substituted-4-chloroisocoumarins[a].

| Inhibitor | HLE[b] | PPE[c] | Cat G[d] | ChyT[e] | RMCP II[f] | SGPA[g] |
|---|---|---|---|---|---|---|
| isocoumarin | | | | | | |
| 3-isobutyloxy-4-chloroisocoumarin | 9500 | NI[j] | 190 | 750 | 920 | 6400 |
| 3-benzyloxy-4-chloroisocoumarin | 1525 | 6 | 1140 | 16000[k] | 9600 | 5500 |
| 3-(4-fluorobenzyloxy)-4-chloroisocoumarin | 2300 | NI | 216 | 32000[l] | 3200 | 3350 |
| 7-nitro-3-methoxy-4-chloroisocoumarin | 2580 | 580 | | | | |
| 7-nitro-3-ethoxy-4-chloroisocoumarin | 2800 | 1300 | NI | 4300 | 7000 | 2700 |
| 7-nitro-3-benzyloxy-4-chloroisocoumarin | | | 2600 | 10500 | 10500 | |
| 7-amino-3-methoxy-4-chloroisocoumarin | 14000 | 1035 | 17 | 108 | 130 | 40 |
| 7-amino-3-ethoxy-4-chloroisocoumarin | 9420 | 700 | 195 | 274 | 876 | 216 |
| 7-(Tos—Phe—NH)—4-chloro-3-methoxy-isocoumarin | 190000 | 6480 | 195 | 274 | NI | NI |

[a]Conditions were 0.1 M Hepes, 0.5 M NaCl, pH 7.5, 10% Me$_2$SO, at 25° C. Rate constants were obtained by the incubation method unless otherwise noted. An aliquot of inhibitor was added to a solution of enzyme and aliquots removed with time and assayed for remaining enzymatic activity. The first order rate constants, $k_{obsd}$, were obtained from plots of ln (v/v$_o$) versus times. The units of $k_{obsd}/[I]$ are M$^{-1}$s$^{-1}$.
[b]Inhibitor concentrations were from 0.007 to 0.011 mM.
[c]Inhibitor concentrations were from 0.037 to 0.011 mM.
[d]Inhibitor concentrations were from 0.113 to 0.009 mM.
[e]Inhibitor concentrations were from 0.013 to 0.098 mM.
[f]Inhibitor concentrations were from 0.030 to 0.009 mM.
[g]Inhibitor concentrations were from 0.086 to 0.005 mM.
[h]Progress curve method with [I] = 175-600 nM.
[i]Progress curve method with [I] = 0.012 mM.
[j]NI, no inactivation
[k]Progress curve method with [I] = 0.0003-0.0017 mM.
[l]Progress curve method with [I] = 0.0012 mM.

The spontaneous hydrolysis rates of many of these substituted isocoumarins in buffer solution have been measured and are summarized in Table III. The hydrolysis rates are dependent upon the composition of the buffer. In general, these isocoumarins are more stable in phosphate buffered saline (pH 7.4) than in Hepes buffer (pH 7.5). The most stable inhibitor studied was 7-amino-3-methoxy-4-chloroisocoumarin while the most unstable was 3,4-dichloroisocoumarin. In addition, 7-amino-3-methoxy-4-chloroisocoumarin is quite stable in albumin (0.4 mg/ml) while 3,4-dichloroisocoumarin decomposed rapidly upon addition to albumin (0.4 mg/ml). The 3-alkoxy-4-chloroisocoumarins are intermediate in stability. These compounds are significantly more stable than other serine protease inhibitors such as aza-peptides and sulfonyl fluorides.

TABLE III

Half-lives for Spontaneous Hydrolysis of Substituted Isocoumarins in Buffer Solution[a].

| Compound | t$_{\frac{1}{2}}$ (min) Hepes pH 7.5[b] | Phosphate pH 7.4[c] |
|---|---|---|
| 3-chloroisocoumarin | 140 | 360 |
| 3,4-dichloroisocoumarin | 18 | 48 |
| 3-ethoxy-4-chloro-isocoumarin | 144 | |
| 3-benzyloxy-4-chloro-isocoumarin | 68 | |
| 3-(4-fluorobenzyloxy)-4-chloroisocoumarin | 53 | |
| 7-amino-3-methoxy-4-chloroisocoumarin | 195 | 820 |

TABLE III-continued

Half-lives for Spontaneous Hydrolysis of Substituted Isocoumarins in Buffer Solution[a].

| Compound | t$_{\frac{1}{2}}$ (min) Hepes pH 7.5[b] | Phosphate pH 7.4[c] |
|---|---|---|
| 4-chloroisocoumarin | | |

[a]Spontaneous hydrolysis rates were measured spectrophotometrically by monitoring the decrease in absorbance due to the isocoumarin ring system (wavelength range: 385-325 nm) and these rates converted to half-lives using the first order rate law.
[b]Conditions were: 0.1 M Hepes buffer, 0.5 M NaCl, 10% Me$_2$SO at 25° C.
[c]Conditions were: 0.02 M K$_2$HPO$_4$, 0.15 M NaCl, 10% Me$_2$SO at 25° C.

It has been found that certain heterocyclic compounds will inhibit serine proteases such as elastase and chymotrypsin by blocking the active site of the enzyme. The compounds of this invention are 3-substituted-7-substituted-(1H)2-benzopyran-1,4(3H)-diones. The unsubstituted (1H)2-benzopyran-1,4(3H)-dione has been prepared previously for other purposes (cf. Knott, J. Chem. Soc., pp 402-410 (1963). The heterocyclic serine protease inhibitors of this invention have the following structural formula:

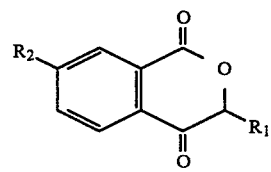

wherein $R_1$ is selected from the group consisting of H, halogen, $C_{1-6}$ alkyl, $C_{1-6}$ alkyl with an attached phenyl, $C_{1-6}$ fluorinated alkyl, $C_{1-6}$ alkoxy, $C_{1-6}$ fluorinated alkoxy, $C_{1-6}$ alkoxy with an attached phenyl, benzyloxy, 4-fluorobenzyloxy, -OCH$_2$C$_6$H$_5$-R' (2-substituent), -OCH$_2$C$_6$H$_5$-R' (3-substituent), -OCH$_2$C$_6$H$_5$-R' (4-substituent), -OCH$_2$C$_6$H$_4$-R$_2$' (2,3-substituents), -OCH$_2$C$_6$H$_4$-R$_2$' (2,4-substituents), -OCH$_2$C$_6$H$_4$-R$_2$' (2,5-substituents), -OCH$_2$C$_6$H$_4$-R$_2$' (2,6-substituents), -OCH$_2$C$_6$H$_4$-R$_2$' (3,4-substituents), and -OCH$_2$C$_6$H$_4$-R$_2$' (3,5-substituents), R' is selected from the group consisting of H, halogen, trifluoromethyl, NO$_2$, cyano, methyl, methoxy, acetyl, carboxyl, OH, and amino, $R_2$ is selected from the group consisting of H, OH, NH$_2$, NO$_2$, halogen, -NH-C(NH)-NH$_2$, -C(NH)NH$_2$, $C_{1-6}$ alkoxy, $C_{1-6}$ fluorinated alkoxy, $C_{1-6}$ alkyl, and $C_{1-6}$ alkylamino.

The following novel compounds are representative of this invention:
(1H)2-benzopyran-1,4(3H)-dione,
3-ethyl-(1H)2-benzopyran-1,4(3H)-dione,
3-propyl-(1H)2-benzopyran-1,4(3H)-dione,
3-phenyl-(1H)2-benzopyran-1,4(3H)-dione.

These structures inhibit serine proteases by forming relatively stable acyl enzymes. HL elastase (0.0004 mM) is totally inactivated by 3-propyl-1H-2-benzopyran-1,4(3H)-dione (0.143 mM) while chymotrypsin (0.002 mM) is totally inhibited by this compound at a concentration of 0.2 mM. The unsubstituted 1H-2-benzopyran-1,4(3H)-dione is a less effective inhibitor than the propyl derivative towards HL elastase and chymotrypsin. These compounds are more potent inhibitors of HL elastase and chymotrypsin than cathepsin G and PP elastase. As with the substituted isocoumarins mentioned earlier, the specificity of these structures towards a particular serine protease can be partially controlled by the nature of the substituent groups ($R_1$ and $R_2$).

To use the above identified inhibitors in vitro, they are dissolved in an organic solvent such as dimethylsulfoxide or ethanol and are added to an aqueous solution containing the protease which is to be inhibited such that the final concentration of organic solvent is 25% or less. The inhibitors may also be added as solids or in suspension.

The serine protease inhibitors of this invention would be useful in a variety of experimental procedures where proteolysis is a significant problem. Inclusion of these inhibitors in radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast and E. coli and would result in a more easily purified cloned product in higher yield.

It is well known in the literature that in vitro activity of elastase inhibitors correlates with in vivo activity in animal models of emphysema. Thus the novel inhibitors described here should be useful for the treatment of emphysema. Elastase inhibitors have been used orally, by injection or by instillation in the lungs in animal studies (cf. Powers, Am. Rev. Respir. Dis., 127, s54–s58 (1983) and references cited therein). The inhibitors described above can be used by any of these routes. The article by Powers (Am. Rev. Respir. Dis., 127, s54–s58 (1983)) is incorporated herein by reference.

Several other diseases also involve tissue destruction by proteases such as elastase-like and chymotrypsin-like enzymes (cf. Powers, Ad. in Chem., 198, 347–367 (1982)). This article by Powers is incorporated herein by reference. The other diseases include pancreatitis, inflammation, and adult respiratory syndrome. Although correlations between in vitro activity of elastase and chymotrypsin inhibitors and in vivo activity in animal models have not yet be made for these diseases, it is likely that such correlations will be made shortly. And the novel inhibitors can then be used in any cases where such correlations are made.

The following examples are given to illustrate the invention and are not intended to limit it in any manner.

EXAMPLE 1

Preparation of 3-Benzyloxy-4-Chloroisocoumarin

Homophthalic acid (0.5 g, 2.78 mmoles) was placed in benzyl alcohol (5 mL) and 2 drops of concentrated sulfuric acid added. The reaction mixture was heated at 60 to 80 degrees centigrade for 45 min, poured into 50 mL of ice-cold NaHCO$_3$ (4%) and washed with three portions of ethyl acetate (50 mL). The aqueous layer was acidified to pH 2 with concentrated HCl and allowed to stand overnight. The precipitate was filtered and dried to give benzyl 2-carboxyphenyl acetate (300 mg) as a white solid: $R_f$=0.7 (chloroform/methanol (9/1)). The benzyl 2-carboxyphenyl acetate (300 mg) was dissolved in benzene (7 mL) and PCl$_5$ (474 mg, 2.28 mmoles) added. The reaction mixture was refluxed for 45 min and the benzene and POCl$_3$ removed by rotary evaporation. Approximately one-half of the residue was chromatographed on silica gel using benzene as the eluent to give 3-benzyloxy-4-chloroisocoumarin (125 mg) as a pale yellow solid: mp 92 deg centigrade, $R_f$=0.63 (benzene). Anal. Calcd. for C$_{16}$H$_{11}$O$_3$Cl: C, 67.02; H, 3.84. Found: C, 66.83; H, 3.86.

EXAMPLE 2

Preparation of 3-(4-Fluorobenzyloxy)-4-Chloroisocoumarin

Homophthalic acid (4.0 g) was added to a solution containing 4-fluorobenzyl alcohol (10 mL), benzene (10 mL) and H$_2$SO$_4$ (3 drops) and the mixture refluxed at 80 degrees centigrade for 2 h. The reaction mixture was diluted with ethyl acetate (125 mL) and washed with 4% NaHCO$_3$ (500 mL). The aqueous layer was acidified to pH 3 with concentrated HCl and the solution placed in the refrigerator overnight. The crystals which formed upon cooling were filtered, dissolved in methylene chloride, and dried over magnesium sulfate. The (4-fluorobenzyl) 2-carboxyphenyl acetate was collected from methylene chloride as a white solid (800 mg) and was used without further purification. The (4-fluorobenzyl) 2-carboxyphenyl acetate (0.8 g) was added slowly to a solution of PCl$_5$ (1.16 g) in benzene (10 mL) and the mixture refluxed at 80 degrees centigrade for 45 min. The benzene was removed, and the residue dissolved in diethyl ether, and filtered. The filtrate was concentrated and collected with isopropyl ether as pale yellow needles (500 mg): mp 127, IR (CH$_2$Cl$_2$) 1743 cm$^{-1}$. Anal. Calcd. for C$_{16}$H$_{10}$ClFO$_3$: 63.07; H, 3.31. Found: C, 62.82; H, 3.36.

EXAMPLE 3

Preparation of 3-Isobutyloxy-4-Chloroisocoumarin

Homophthalic acid (4.0 g) was placed in isobutanol (25 mL) and 3 drops of $H_2SO_4$ added. The reaction mixture was heated for 1 h at 100–110 degrees centigrade, poured into 120 mL of ethyl acetate, and washed with 4% $NaHCO_3$ (15 mL, ×5). The combined aqueous washes were acidified to pH 3 using concentrated HCl and the resulting precipitate collected. The precipitate was dried to give isobutyl 2-carboxyphenyl acetate as a white solid (1.8 g). The isobutyl 2-carboxyphenyl acetate (0.7 g) was placed in a mixture of $PCl_5$ (1.23 g) and benzene (20 mL) and the mixture heated at reflux for 30 min. The solvent was removed and the residue purified by silica gel chromatography using benzene as the eluent to give product as pale yellow needles (338 mg); mp 48; IR $(CH_2Cl_2)$ 1740 $cm^{-1}$. Anal Calcd. for $C_{13}H_{13}ClO_3$: C, 61.79; H, 5.19. Found: C, 61.64; H, 5.22.

EXAMPLE 4

Preparation of 7-Nitro-3-Benzyloxy-4-Chloroisocoumarin

4-Nitro-homophthalic acid (5.0 g) was suspended in benzyl alcohol (50 mL) and $H_2SO_4$ (3 drops) added. The reaction mixture was heated at 70–80 degrees centigrade for 45 min, diluted into 100 mL of ethyl acetate, and washed with 1 L of 4% $NaHCO_3$. The aqueous layers were combined, acidified to pH 3 using concentrated HCl, and extracted with 500 mL of ethyl acetate. The ethyl acetate layer was dried over magnesium sulfate and concentrated to give ca. 4 g of crude product, which was titurated with isopropyl ether to give 3.8 grams of benzyl 2-carboxy-4-nitrophenyl acetate: mp. 171–172. Anal. Calcd. for $C_{16}H_{13}NO_6$: C, 60.96; H, 4.18. Found : C, 60.86; H, 4.18. The benzyl 2-carboxy-4-nitrophenyl acetate (3.0 g) was slowly added to a solution of $PCl_5$ (4.35 g) in benzene (150 mL) and the reaction mixture stirred overnight at 25 degrees centigrade. The benzene solution was washed with 1.2 L of water, dried over magnesium sulfate and concentrated to give a crude yellow solid. The crude product was titurated with isopropyl ether to give 575 mg of a yellow solid which was purified further by silica gel chromatography using methylene chloride as the eluent. The pure product was crystallized from methylene chloride to give 500 mg of yellow needles: mp 153–154 dec, IR $(CH_2Cl_2)$ 1785 $cm^{-1}$, 1622 $cm^{-1}$. Anal Calcd. for $C_{16}H_{10}ClNO_5$: C, 57.94; H, 3.04; N, 4.22. Found: C, 58.04; H, 3.09; N, 4.18.

EXAMPLE 5

Preparation of 4-Chloro-7-Nitro-3-(2-Phenethoxy)isocoumarin

4-Nitrohomophthalic acid (6.0 g, 26.5 mmoles) was suspended in 2-phenylethanol (20 mL), $H_2SO_4$ (3 drops) added, and the reaction mixture heated at 120°–130° C. for 3.5 h. The mixture was diluted with ethyl acetate (200 mL) and washed with 4% $NaHCO_3$ (2×300 mL). Thin layer chromatography indicated that the product was contained primarily in the ethyl acetate layer. After concentration of the ethyl acetate layer, the solid was titurated with isopropyl ether to give the 2-phenylethyl ester of 2-carboxy-4-nitrophenylacetic acid (2.0 g) as a tan solid and was used without further purification. The ester (1.3 g, 3.9 mmoles) was added slowly to a solution of $PCl_5$ (2.05 g, 9.9 mmoles) in benzene (30 mL) and the mixture refluxed at 80° C. for 1 h. The benzene was removed and the residue titurated with petroleum ether. The crude product was purified by silica gel chromatography using benzene as the eluent to give 4-chloro-7-nitro-3-(2-phenethoxy)isocoumarin (0.1 g) as an orange solid: mp 95°–100° C. (dec), one spot on TLC, $R_f^2 = 0.5$; IR (nujol) 1752 $cm^{-1}$. Anal. Calcd. for $C_{17}H_{12}ClNO_5$: C,59.05; H,3.50. Found: C, 58.9; H, 3.55.

EXAMPLE 6

Preparation of 7-Amino-4-Chloro-3(2-Phenethoxy)isocoumarin

The 4-chloro-7-nitro-3-(2-phenethoxy)isocoumarin (50 mg, 0.14 mmoles) was dissolved in absolute ethanol (50 mL) and hydrogenated using Pd-C (50 mg) for 2 h. After filtering over celite, the solvent was removed and the residue chromatographed on silica gel using methylene chloride as the eluent to give 7-amino-4-chloro-3(2-phenethoxy)isocoumarin (35 mg) as yellow plates: mp 105°–107° C; one spot on TLC, $R_f^3 = 0.45$; IR$(CH_2Cl_2)$ 1745 $cm^{-1}$; mass spectrum m/e 315 (M+). Anal. Calcd. for $C_{17}H_{14}ClNO_3$: C, 64.66; H, 4.47. Found: C, 64.56; H, 4.51.

EXAMPLE 7

Preparation of 7-(N-Tosyl-Phenylalanylamino)-4-Chloro-3-Methoxyisocoumarin

N-Tosyl-phenylalanine acid chloride (77 mg, 0.3 mmoles) and 7-amino-4-chloro-3-methoxyisocoumarin (50 mg, 0.2 mmoles) were suspended in a mixture of methylene chloride/tetrahydrofuran (1:1) and triethylamine (0.037 mL, in 2 mL of methylene chloride) added dropwise with stirring. After stirring at 25° C. for 2 h, the reaction solvents were removed and the residue dissolved in ethyl acetate. After washing with 10% citric acid (3×30 mL) and 4% $NaHCO_3$ (2×30 mL), the ethyl acetate layer was dried over magnesium sulfate and concentrated. The crude product was purified by silica gel chromatography using a 1% mixture of methanol in methylene chloride and the 7-(N-tosyl-phenylalanylamino)-4-chloro-3-methoxyisocoumarin (22 mg) collected from methanol/isopropyl ether as a pale yellow solid: mp 222°–224° C. (dec); one spot on TLC, $R_f^3 = 0.3$; IR (nujol) 1750 $cm^{-1}$; mass spectrum m/e 527 (M+1). Anal. Calcd. for $C_{26}H_{23}ClN_2O_6S\frac{1}{2}H_2O$: C, 58.26; H, 4.53. Found: C, 58.28; H, 4.50.

EXAMPLE 8

Preparation of 3-Propyl-1H-2-Benzopyran-1,4(3H)-dione.

A solution of 3-bromo,3-(1-bromobutyl)-1(3H)-isobenzofuranone (500 mg) in $Me_2SO$ (15 mL) was added dropwise to a solution of 0.1 M Hepes buffer (pH 7.5, 50 mL) containing 0.5 M NaCl and $Me_2SO$ (35 mL). The mixture was stirred at 25 degrees centigrade, diluted with water (100 mL) and extracted with ethyl acetate (50 mL, ×2). The extracts were combined, washed with water (50 mL, ×5), dried over magnesium sulfate, and concentrated under reduced pressure. The residue was chromatographed on silica gel using benzene as the eluent to give the product as a white solid (170 mg): mp 44–45 degrees centigrade; IR (nujol), 1730, 1700 $cm^{-1}$. Anal. Calcd. for $C_{12}H_{12}O_3$: C, 70.57; H, 5.92. Found: C, 70.55; H, 5.96.

Other illustrative examples are given in references cited below: 3-chloroisocoumarin: Davies and Poole, J. Chem. Soc., pp 1616–1620 (1928); 3,4-dichloroisocoumarin: Milevskaya, Belinskaya, and Yagupol'skii, Zhur. Org. Khim. 9, pp 2145–2149, (1973); 3-methoxy-4-chloroisocoumarin and 3-ethoxy-4-chloroisocoumarin: Tirodkar and Usgaonkar, Ind. J. Chem. 7, pp 1114–1116, (1969); 7-nitro-3-methoxy-4-chloroisocoumarin and 7-amino-3-methoxy-4-chloroisocoumarin: Choksey and Usgaonkar, Ind. J. Chem. 14B, pp 596–598, (1976).

What is claimed is:

1. A process for the inhibition of the enzymatic activity of serine proteases comprising the step of adding to a medium containing the protease that amount of inhibitor effective to inhibit said activity having the following structure:

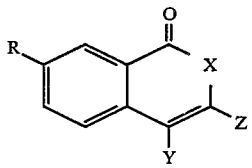

wherein

X is selected from the group consisting of O, and S,

Z is selected from the group consisting of H, halogen, $C_{1-6}$ alkyl, $C_{1-6}$ alkyl with an attached phenyl, $C_{1-6}$ fluorinated alkyl, $C_{1-6}$ alkoxy, $C_{1-6}$ fluorinated alkoxy, $C_{1-6}$ alkoxy with an attached phenyl, benzyloxy, 4-fluorobenzyloxy, -OCH$_2$C$_6$H$_5$-R' (2-substituent), -OCH$_2$C$_6$H$_5$-R' (3-substituent), -OCH$_2$C$_6$H$_5$-R' (4-substituent), -OCH$_2$C$_6$H$_4$-R$_2$' (2,3-substituents), -OCH$_2$C$_6$H$_4$-R$_2$' (2,4-substituents), -OCH$_2$C$_6$H$_4$-R$_2$' (2,5-substituents), -OCH$_2$C$_6$H$_4$-R$_2$' (2,6-substituents), -OCH$_2$C$_6$H$_4$-R$_2$' (3,4-substituents), and -OCH$_2$C$_6$H$_4$-R$_2$' (3,5-substituents), R' is selected from the group consisting of H, halogen, trifluoromethyl, NO$_2$, cyano, methyl, methoxy, acetyl, carboxyl, OH, and amino, Y is selected from the group consisting of H, halogen, trifluoromethyl, methyl, OH, and methoxy, R is selected from the group consisting of H, OH, NH$_2$, NO$_2$, halogen, -NH-C(NH)-NH$_2$, -C(NH)NH$_2$, $C_{1-6}$ alkoxy, $C_{1-6}$ fluorinated alkoxy, $C_{1-6}$ alkyl, $C_{1-6}$ alkylamino, M-AA, and M-NH, wherein AA is selected from the group consisting of alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, alpha-aminobutyric acid, epsilon-aminocaproic acid, citrulline, hydroxyproline, ornithine, and sarcosine.

wherein M is selected from the group consisting of hydrogen, lower alkanoyl having 1 to 6 carbons, carboxylalkanoyl, hydroxyalkanoyl, amino-alkanoyl, benzene sulfonyl, tosyl, benzoyl, and lower alkyl sulfonyl having 1 to 6 carbons.

2. A process for the inhibition of enzymatic activity of serine proteases comprising the step of adding to a medium containing the protease that amount of inhibitor effective to inhibit said activity having the following structure:

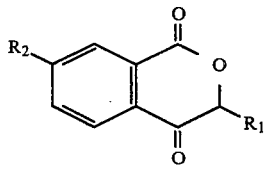

wherein

R$_1$ is selected from the group consisting of H, halogen, $C_{1-6}$ alkyl, $C_{1-6}$ alkyl with an attached phenyl, $C_{1-6}$ fluorinated alkyl, $C_{1-6}$ alkoxy, $C_{1-6}$ fluorinated alkoxy, $C_{1-6}$ alkoxy with an attached phenyl, benzyloxy, 4-fluorobenzyloxy, -OCH$_2$C$_6$H$_5$-R' (2-substituent), -OCH$_2$C$_6$H$_5$-R' (3-substituent), -OCH$_2$C$_6$H$_5$-R' (4-substituent), -OCH$_2$C$_6$H$_4$-R$_2$' (2,3-substituents), -OCH$_2$C$_6$H$_4$-R$_2$' (2,4-substituents), -OCH$_2$C$_6$H$_4$-R$_2$' (2,5-substituents), -OCH$_2$C$_6$H$_4$-R$_2$' (2,6-substituents), -OCH$_2$C$_6$H$_4$-R$_2$' (3,4-substituents), and -OCH$_2$C$_6$H$_4$-R$_2$' (3,5-substituents), R' is selected from the group consisting of H, halogen, trifluoromethyl, NO$_2$, cyano, methyl, methoxy, acetyl, carboxyl, OH, and amino, R$_2$ is selected from the group consisting of H, OH, NH$_2$, NO$_2$, halogen, -NH-C(NH)-NH$_2$, -C(NH)NH$_2$, $C_{1-6}$ alkoxy, $C_{1-6}$ fluorinated alkoxy, $C_{1-6}$ alkyl, and $C_{1-6}$ alkylamino.

* * * * *